US012400321B2

(12) United States Patent
Feng et al.

(10) Patent No.: US 12,400,321 B2
(45) Date of Patent: Aug. 26, 2025

(54) CLASSIFYING NEUROLOGICAL DISEASE STATUS USING DEEP LEARNING

(71) Applicant: The Trustees of Columbia University in the City of New York, New York, NY (US)

(72) Inventors: Xinyang Feng, New York, NY (US); Frank Provenzano, New York, NY (US); Scott A. Small, Millerton, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 562 days.

(21) Appl. No.: 17/514,260

(22) Filed: Oct. 29, 2021

(65) Prior Publication Data

US 2022/0051801 A1    Feb. 17, 2022

Related U.S. Application Data

(63) Continuation of application No. PCT/US2020/030617, filed on Apr. 30, 2020.

(60) Provisional application No. 63/017,304, filed on Apr. 29, 2020, provisional application No. 62/840,633, filed on Apr. 30, 2019.

(51) Int. Cl.
*G06T 7/00* (2017.01)
*G06F 18/24* (2023.01)

(52) U.S. Cl.
CPC ............ *G06T 7/0012* (2013.01); *G06F 18/24* (2023.01); *G06T 2207/20084* (2013.01)

(58) Field of Classification Search
CPC .................... G06T 7/0012; G06T 2207/22084
See application file for complete search history.

(56) References Cited

U.S. PATENT DOCUMENTS

| 10,646,156 | B1* | 5/2020 | Schnorr | G16H 30/40 |
| 2014/0313345 | A1* | 10/2014 | Conard | G06V 20/10 348/169 |
| 2017/0046616 | A1 | 2/2017 | Socher et al. | |
| 2017/0249534 | A1* | 8/2017 | Townsend | G06V 10/82 |
| 2017/0364757 | A1 | 12/2017 | Rajabizadeh et al. | |
| 2018/0262291 | A1* | 9/2018 | Doster | G06N 3/045 |
| 2018/0276333 | A1* | 9/2018 | Njie | G16B 5/00 |
| 2018/0285510 | A1* | 10/2018 | Lutich | G03F 1/36 |
| 2019/0033415 | A1* | 1/2019 | Sofka | A61B 5/7267 |

(Continued)

OTHER PUBLICATIONS

Nontawat Pattanajak and Hossein Malekmohamadi, Improving a 3-D Convolutional Neural Network Model Reinvented from VGG16 with Batch Normalization, 2019, IEEE SmartWorld (Year: 2019).*

(Continued)

*Primary Examiner* — Kevin Ky
(74) *Attorney, Agent, or Firm* — Hunton Andrews Kurth LLP

(57) ABSTRACT

A method for classifying neurological disease status is described. The method includes acquiring, by a data preprocessor logic, patient image data. The method further includes generating, by a trained artificial neural network (ANN), a classification output based, at least in part, on the patient image data. The classification output corresponds to a neurological disease status of the patient. The trained ANN is trained based, at least in part, on longitudinal source data.

22 Claims, 4 Drawing Sheets

(56) References Cited

U.S. PATENT DOCUMENTS

| | | | |
|---|---|---|---|
| 2019/0114544 A1* | 4/2019 | Sundaram | G06F 18/2155 |
| 2019/0114547 A1* | 4/2019 | Jaganathan | G16B 40/00 |
| 2020/0293032 A1* | 9/2020 | Wang | G01R 31/086 |
| 2020/0320634 A1* | 10/2020 | Dance | G06N 20/00 |
| 2021/0007603 A1* | 1/2021 | Huddleston | A61B 5/4082 |
| 2022/0051801 A1* | 2/2022 | Feng | G06T 7/0012 |

OTHER PUBLICATIONS

U.S. Appl. No. 62/840,633 (Year: 2019).*
International Search Report and Written Opinion for International Patent Application No. PCT/US2020/030617 mailed on Jul. 21, 2020.

* cited by examiner

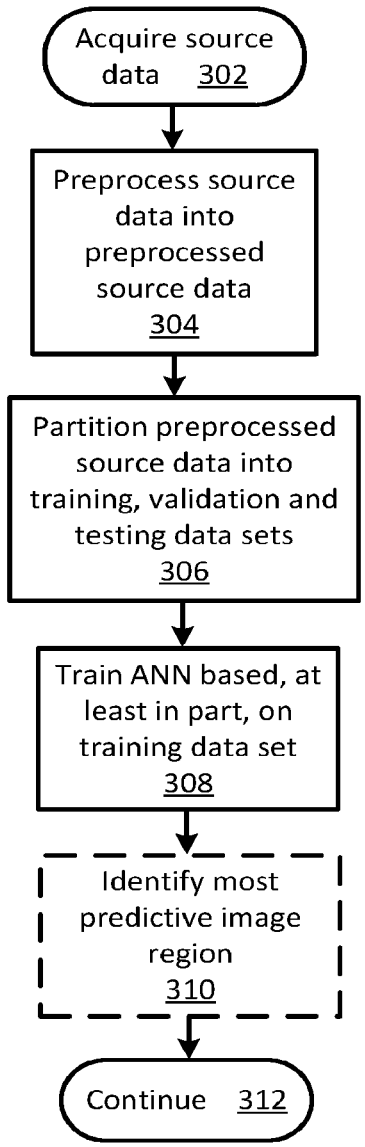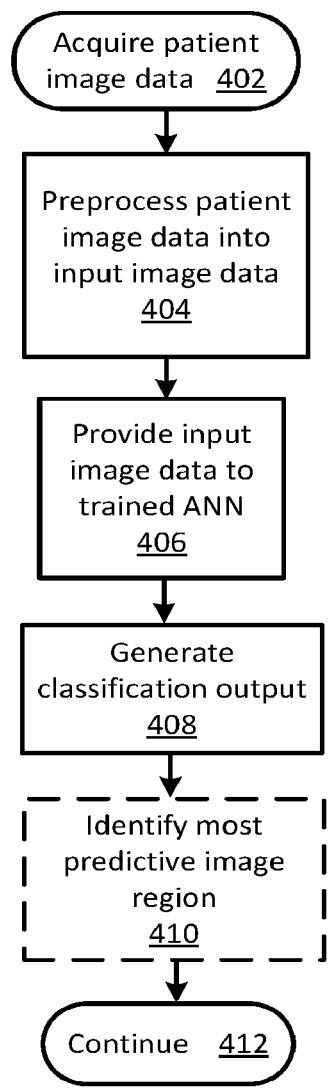
FIG. 3
FIG. 4

CLASSIFYING NEUROLOGICAL DISEASE STATUS USING DEEP LEARNING

CROSS REFERENCE TO RELATED APPLICATION(S)

This application is a continuation of International Patent Application No. PCT/US2020/030617 filed on Apr. 30, 2020, which published as International Publication No. WO 2020/223434 on Nov. 5, 2020, which relates to and claims priority from U.S. Provisional Patent Application No. 62/840,633, filed Apr. 30, 2019, and U.S. Provisional Patent Application No. 63/017,304, filed Apr. 29, 2020, the entire disclosures of which are incorporated herein by reference.

FIELD

The present disclosure relates to classifying neurological disease status, in particular to classifying neurological disease status using deep learning.

BACKGROUND

Alzheimer's disease (AD) is a progressive neurodegenerative disease responsible for a majority of cases of dementia. Because of the degenerative nature of the illness and the current lack of a cure, research has focused on developing techniques for early diagnosis and intervention. Given an accurate early detection system, future treatments may have a relatively greater impact if administered earlier in the disease progression. Recent studies have demonstrated that magnetic resonance imaging (MRI) may be useful in diagnosing AD, in recognizing mild cognitive impairment (MCI) (the corresponding prodromal stage), and in categorizing biomarkers associated with neurodegeneration in AD.

Among different brain MRI modalities, T1-weighted (T1w) structural MRI is currently the most widely available. MM enjoys the additional benefit of being relatively standardized across scanners and protocols. Consequently, diagnosis algorithms based on T1w structural MRIs are appealing as a potential tool to assist in disease screening given the wide availability of research scans for training models, and the ubiquity of MRI scanners in the world.

Following breakthroughs in computer vision (CV), deep learning techniques have emerged as popular tools for analyzing medical images. On standard CV tasks such as classification, object detection, and semantic segmentation, deep learning techniques based on convolutional neural networks (CNNs) have achieved dominance. For specific tasks with abundant training data—and when the training data and test data are sampled from the same distribution, these models often achieve human-level performance or better. Moreover, due to the generality of the methods, the availability of open source code, and the wide availability of specialized computer hardware for accelerating these algorithms, they may be easily adopted by practitioners. Over the last few years, these techniques have been applied in image-aided medical diagnosis. Successful applications of deep learning in medical imaging include segmenting images produced from electron microscopy, detecting diabetic retinopathy from two dimensional (2D) retinal fundus photographs, and recognizing skin cancer from photographs.

Learning from three dimensional (3D) scans, such as MRI, presents a number of additional challenges. While the number of voxels corresponding to the 3D volume representing a single patient can be large, there is generally one label per scan, raising technical questions about how to prevent overfitting. Further, despite generating relatively accurate predictions, deep learning has been described as a "black box" because of the challenges associated with attempts to explain or interpret the classifications produced by various deep learning techniques. The topic has been intensely debated and researched in connection with critical settings like medical diagnosis, predictive policing, and other impactful automated decision-making scenarios where accountability is a concern.

SUMMARY

In some embodiments, a method for classifying neurological disease status is provided. The method includes acquiring, by a data preprocessor logic, patient image data. The method further includes generating, by a trained artificial neural network (ANN), a classification output based, at least in part, on the patient image data. The classification output corresponds to a neurological disease status of the patient. The trained ANN is trained based, at least in part, on longitudinal source data.

In some embodiments, the method further includes preprocessing, by the data preprocessor logic, the patient image data to yield input image data. The classification output is generated based, at least in part, on the input image data.

In some embodiments, the method further includes identifying, by localization logic, a most predictive image region based, at least in part, on an ANN parameter associated with the trained ANN.

In some embodiments of the method, the longitudinal source data includes a plurality of source image data sets from a same selected patient. The longitudinal source data is partitioned into training, validation and test data, and the partitioning occurs at a level of the same selected patient.

In some embodiments of the method, the image data is selected from the group including magnetic resonance imaging (MRI) image data, MRI T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, and single-photon emission computerized tomography (SPECT) image data.

In some embodiments of the method, the neurological disease is selected from the group including neurodegenerative diseases and non-neurodegenerative diseases. Each neurodegenerative disease is selected from the group including Alzheimer's disease, amyotrophic lateral sclerosis (ALS), frontotemporal dementia (FTD) and Parkinson's disease. Each non-neurodegenerative disease is selected from the group including cerebrovascular disease, epilepsy, and stroke.

In some embodiments of the method, the neurological disease corresponds to Alzheimer's disease and the classification output is selected from the group including Alzheimer's disease (AD), prodromal AD, mild cognitive impairment (MCI) and cognitively normal (CN).

In some embodiments of the method, the ANN is a selected from the group including CNN (convolutional neural network), VGGNet (Visual Geometry Group neural network), ResNet (residual network), and DenseNet (densely connected convolutional networks).

In some embodiments of the method, the ANN is a three-dimensional convolutional neural network (3D CNN), the 3D CNN including a number, N, CNN stages coupled in series. Each stage includes a first 3D convolutional layer, a second 3D convolutional layer, a batch normalization layer, an activation layer, and a pooling layer, coupled in series. The 3D CNN further includes a flattening layer, a fully connected layer and a sigmoid activation function layer.

In some embodiments, a neurological disease classifier system is provided. The system includes a data preprocessor logic configured to acquire patient image data. The system further includes a trained artificial neural network (ANN) configured to generate a classification output based, at least in part, on the patient image data. The classification output corresponds to a neurological disease status of the patient. The trained ANN is trained based, at least in part, on longitudinal source data.

In some embodiments of the system, the data preprocessor logic is further configured to preprocess the patient image data to yield input image data and the classification output is generated based, at least in part, on the input image data.

In some embodiments, the system further includes localization logic configured to identify a most predictive image region based, at least in part, on an ANN parameter associated with the trained ANN.

In some embodiments of the system, the longitudinal source data includes a plurality of source image data sets from a same selected patient. The longitudinal source data is partitioned into training, validation and test data, and the partitioning occurs at a level of the same selected patient.

In some embodiments of the system, the image data is selected from the group including magnetic resonance imaging (MRI) image data, MRI T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, and single-photon emission computerized tomography (SPECT) image data.

In some embodiments of the system, the neurological disease is selected from the group including neurodegenerative diseases and non-neurodegenerative diseases. Each neurodegenerative disease is selected from the group including Alzheimer's disease, amyotrophic lateral sclerosis (ALS), frontotemporal dementia (FTD) and Parkinson's disease. Each non-neurodegenerative disease is selected from the group including cerebrovascular disease, epilepsy, and stroke.

In some embodiments of the system, the neurological disease corresponds to Alzheimer's disease and the classification output is selected from the group including Alzheimer's disease (AD), prodromal AD, mild cognitive impairment (MCI) and cognitively normal (CN).

In some embodiments of the system, the ANN is a selected from the group comprising CNN (convolutional neural network), VGGNet (Visual Geometry Group neural network), ResNet (residual network), and DenseNet (densely connected convolutional networks).

In some embodiments of the system, the ANN is a three-dimensional convolutional neural network (3D CNN) and the 3D CNN includes a number, N, CNN stages coupled in series. Each stage includes a first 3D convolutional layer, a second 3D convolutional layer, a batch normalization layer, an activation layer, and a pooling layer, coupled in series. The 3D CNN further includes a flattening layer, a fully connected layer and a sigmoid activation function layer.

In some embodiments, a neurological disease classification device is provided. The device includes means to perform any embodiment of the method.

In some embodiments a computer readable storage device is provided. The device has stored thereon instructions that when executed by one or more processors result in the following operations including any embodiments of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein:

FIG. 3 is a flowchart of example ANN training operations consistent with several embodiments of the present disclosure;

FIG. 4 is a flowchart of example neurological disease classification operations consistent with several embodiments of the present disclosure.

DETAILED DESCRIPTION

Figure 1A:
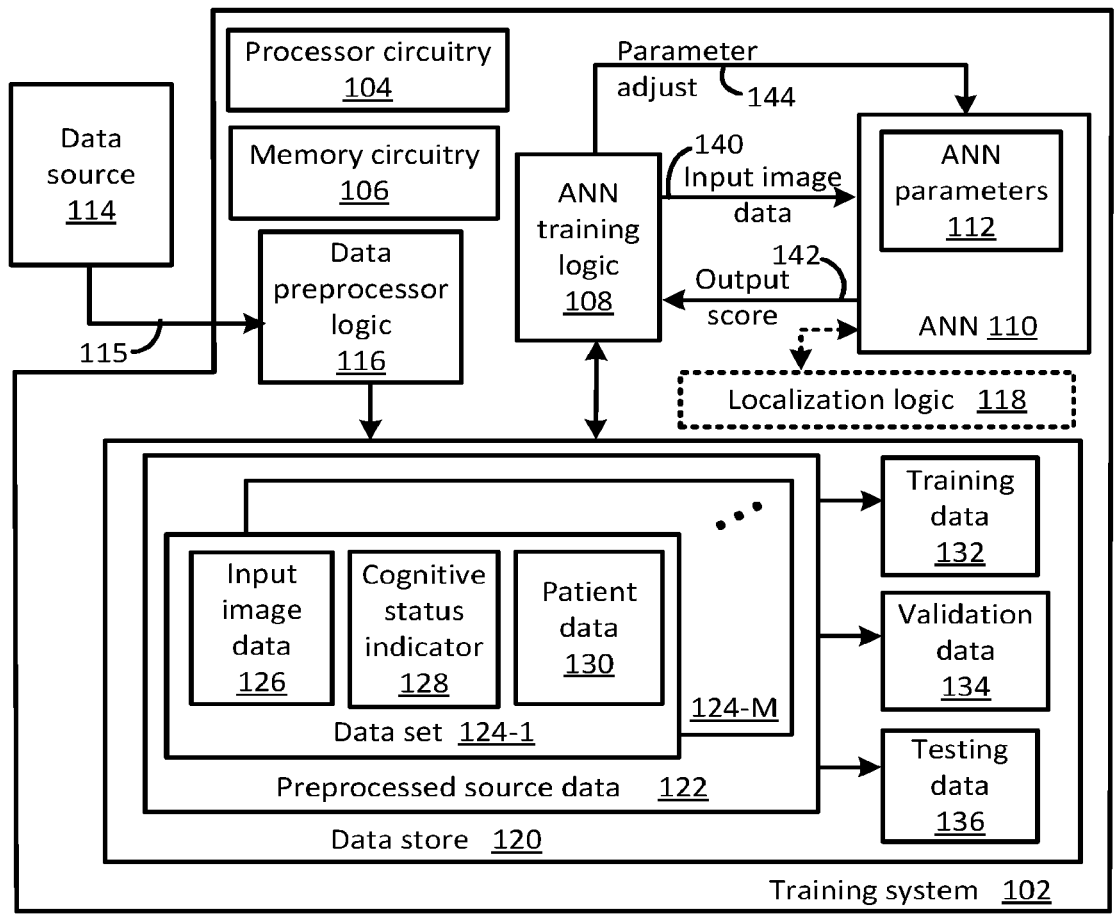
FIG. 1A illustrates a functional block diagram of a training system including an artificial neural network (ANN) consistent with several embodiments of the present disclosure.

Generally, the present disclosure relates to a deep learning method and/or system configured to diagnose neurological disease based, at least in part, on neuroimaging data. A method and/or system is configured to acquire source data that includes image data, cognitive status indicators and patient data for a plurality of patients. In an embodiment, the source data may include longitudinal imaging data from a patient. As used herein, longitudinal image data corresponds to a plurality of image data sets acquired from a same patient over a time period, e.g. a plurality of source image data acquisition sessions.

In some embodiments, the image data may include, but is not limited to, magnetic resonance imaging (MRI) T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, single-photon emission computerized tomography (SPECT) image data, etc.

The method and/or system are configured to partition the source data into training data, validation data and testing data. The partitioning is configured to ensure that longitudinal data from a single patient is included in one partition, e.g., training data, and to thus avoid data leakage. The partitioning is further configured to separate patients into groups without overlap. In other words, the partitioning is configured such that image data from a particular patient is included in only one group.

The method and/or system are further configured to train an artificial neural network (ANN) based, at least in part, on the training data. ANN may include, but is not limited to, CNN (convolutional neural network, e.g., three-dimensional (3D) CNN and/or two-dimensional (2D) CNN), VGGNet (Visual Geometry Group neural network), ResNet (residual network), and DenseNet (densely connected convolutional networks). The trained ANN may then be utilized to classify, i.e., generate a classification output, for a selected patient based, at least in part, on patient image data captured from the selected patient. In an embodiment, the classification output may correspond to an indicator corresponding to a likelihood that the selected patient will develop a neurological disease. Thus, in some embodiments, the classification output may include an output score. Neurological diseases may include neurodegenerative diseases, i.e., with detectable features due to atrophy present in image data, and non-neurodegenerative diseases. Neurodegenerative diseases may include, but are not limited to, Alzheimer's disease, amyotrophic lateral sclerosis (ALS), frontotemporal dementia (FTD), Parkinson's disease, etc. Non-neurodegenerative diseases may include, but are not limited to, cerebrovascular disease, epilepsy, and stroke.

In some embodiments, the trained ANN may be analyzed to identify a most predictive region in an input image data. As used herein, the most predictive region corresponds to a region (or portion) of an image that has a relatively greater effect on the classification output. The most predictive region may then point to a region in the brain that may be associated with the existence and progression of neurological disease.

Thus, a method and/or system, according to the present disclosure, may be configured to expand (i.e., augment) source data (and training data) by including longitudinal data with appropriate partitioning. A trained ANN may then be utilized to predict whether a selected patient is likely to develop a neurological or other disease of the brain and the result may then be utilized to support treatment planning. Identification of a most predictive region may then be utilized to facilitate understanding of the disease itself and/or to reduce "black box" aspects that may be associated with ANNs.

Thus, in some embodiments, systems and methods according to the disclosed subject matter may include a neurological disease diagnosis framework based on a deep ANN model using a structural imaging technique, empowered with the inclusion of longitudinal scans. In one nonlimiting example, the framework, as described herein, demonstrates relatively high classification performance in Alzheimer's disease (AD) versus cognitive normal (CN) using structural MRI. Systems and methods according to the disclosed subject matter demonstrate relatively high accuracy in mild cognitive impairment (MCI) progression prediction applying the model trained on AD vs. CN classification to the MCI subgroup. Through class activation map and rigorous ablation analyses on both slice-level and lobe-level, systems and methods according to the disclosed subject matter pinpoint hippocampal formation as the most predictive regions for AD classification, affirming the prominence of hippocampal formation in AD diagnosis, and demonstrating the importance of regionality even in highly complicated deep neural network models. It may be appreciated that the classification and regional analyses methods according to the present disclosure provide a general framework that may be applied to other disorders and imaging modalities. It may be appreciated that a method and/or system may utilize data with relatively less detail or information from a scanner. Such data may be captured from a shorter scan with fewer slices or from an MRI scanner with relatively lower fidelity than that of conventional scanners.

The dataset used in some embodiments is from the Alzheimer's Disease Neuroimaging Initiative (ADNI).

ADNI is a multisite study that aims to improve clinical trials for the prevention and treatment of Alzheimer's disease (AD). This cooperative effort studies subjects with AD, those who may develop AD, and controls with no signs of cognitive impairment. Researchers at a number of sites in the United States (US) and Canada track the progression of AD in the human brain with neuroimaging, biochemical, and genetic biological markers. This information may help to find better clinical trials for the prevention and treatment of AD. ADNI has developed a set of standardized protocols to allow the comparison of results from multiple centers, and has a data-sharing policy which makes available all of the data to qualified researchers worldwide. The details about the MRI data acquisition can be found in ADNI website. The T1-weighted structural MRI scans utilized herein were preprocessed with the standard Mayo Clinic pipeline. AD diagnosis was based on clinical evaluations.

FIG. 1A illustrates a functional block diagram of a training system 102, including an artificial neural network (ANN) 110 consistent with several embodiments of the present disclosure. ANN 110 may include, but is not limited to, a CNN (e.g., 3D CNN or 2D CNN), VGGNet, ResNet, and DenseNet. In one nonlimiting example, ANN 110 may correspond to a CNN, e.g., a 3D CNN. However, this disclosure is not limited in this regard. Training system 102 includes processor circuitry 104, memory circuitry 106, ANN training logic 108, the ANN 110, data preprocessor logic 116 and data store 120. In some embodiments, training system 102 may include localization logic 118. Training system 102, e.g., data store 120, may further include preprocessed source data 122, as will be described in more detail below.

Processor circuitry 104 may be configured to perform one or more operations of ANN training logic 108, ANN 110, data preprocessor logic 116 and/or localization logic 118. Memory circuitry 106 may be configured to store data store 120 and/or information and/or data associated with operation of ANN 110, ANN training logic 108, data preprocessor logic 116 and/or localization logic 118.

ANN training logic 108 is configured to manage training operations of ANN 110. ANN 110 may be trained based, at least in part, on source data 115 acquired from data source 114. The source data 115 may include a plurality of source data sets. Each source data set may include image data, a cognitive status indicator and corresponding patient data. Image data, i.e., medical image data, may include, but is not limited to, magnetic resonance imaging (MRI) image data, MRI T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, and single-photon emission computerized tomography (SPECT) image data. In one nonlimiting example, for each data set, image data may include an MRI brain scan. In this example, image data may thus include a plurality of voxel intensity values. Cognitive status may include, but is not limited to, cognitively normal, prodromal neurological disease, mild cognitive impairment and neurological disease (e.g., stable or progressive). In one nonlimiting example, the neurological disease may be Alzheimer's disease. A respective unique cognitive status indicator may be associated with each cognitive status. The corresponding patient data may include a unique patient identifier, e.g., an alphanumeric value, associated with each patient whose data is included in the source data 115. The patient identifier may be utilized for partitioning source data and is not related to patient identity. The patient data may further include a time indicator, e.g., a respective time stamp associated with each input image data set.

Each source data set may be preprocessed by, e.g., data preprocessor logic 116, to produce preprocessed source data 122. The preprocessed source data 122 may contain one or more data sets 124-1, ..., 124-M. Each data set, e.g., data set 124-1, may then contain input image data 126, cognitive status indicator 128 and patient data 130. Operations associated with data preprocessing may include, but are not limited to, nonparametric nonuniform intensity normalization (N3) based bias field correction, brain extraction using FreeSurfer, as described herein, and 12 degree of freedom affine registration (using FSL FLIRT (as described herein) with normalized mutual information cost function) to the 1 cubic millimeter ($mm^3$) isotropic MNI152 brain template. In one nonlimiting example, the dimension of the 3D volume is 182×218×182 (LR×AP×SI).

Bias field correction is generally robust, fast, and based on physics models which act as a strong prior. Skull-stripping using FreeSurfer in general provides consistently high quality brain extraction. The registration is to ensure same orientation and roughly same spatial correspondence of different images.

Data preprocessor logic 116 may then be configured to partition the preprocessed source data 122 into training data 132, validation data 134 and testing data 136. The partitions may not overlap. The partitioning may be performed based, at least in part, on the patient data 130, and is configured to avoid data leakage, as will be described in more detail below.

Generally, computer vision datasets may be synthetically augmented by applying random transformations to the existing training images. Such random transformations may include translation, rotation, scaling, etc. However, unlike natural images or those collected from some other medical imaging modalities, where objects of interest might vary in location and rotational orientation, medical images of brains are approximately at the same position through registration, with the brain regions roughly aligned. Thus, in the case of medical images, learning rotational and translational invariances is not well motivated.

There is another form of data augmentation or more precisely "data source" that is specific to medical imaging applications. For longitudinal studies, test-retest studies and just ordinary studies, there may be a plurality of scans per subject (i.e., per patient). By including time as a factor in subject identification, the amount of data can be increased. Including these data sources may be considered a natural form of data augmentation. The corresponding "transformations" in data augmentation may include normal aging or disease progression or both (longitudinal scans with a significant interval between scans), subject re-positioning (scans acquired at different sessions and within a short period of time) and subject motion (scans acquired at the same session). The variability present in the scans or the data coverage in the whole data space decreases in this order.

It may be appreciated that the different time points of a same individual might be at different health or disease stages for that individual. Image data, lying on the verge of different diagnosis, may correspond to informative cases for the classification. Utilizing longitudinal data to augment data available for training, validation and testing, may provide a significant increase in the total amount of data available. For example, using image data (i.e., scans) from different sessions, may provide a significant increase in the amount of data. In one nonlimiting example, including longitudinal date increased the number of image data sets from 796 baseline scans to 4691 scans. Image data captured from a same scanning session may have relatively low variability.

Generally, data augmentation helps to prevent models from overfitting by enriching an original source of data through the addition of variations of these examples perturbed through transformations with respect to which it is desired that the model to be invariant. In typical photographic images, such transformations might include random crops, translations, rotations, and small changes to the color palette. In an embodiment consistent with the present disclosure, the image data may be augmented by including images captured from a same patient across a plurality of sessions. As used herein, session and visit are used interchangeably and mean time period in which image data is captured. As used herein, "scan" and "image data" are used interchangeably and correspond to medical image data, as described herein. In one nonlimiting example, "scan" and "image data" may correspond to MRI image data, i.e., a set of intensity voxels. However, this disclosure is not limited in this regard.

Inclusion of a plurality of scans from a same subject (i.e., patient) raises two potential concerns: data leakage and disease progression. Data leakage may occur when the training data sets and testing data sets contain different scans from the same subject. The ANN might make a prediction by memorizing and retrieving the label (i.e., output score) from the same patent. Such an outcome may result in overoptimistic performance.

The disease progression concern is related to the possibility that a disease status of a patient may change over time, thus affecting subsequent scan data. Thus, the cross-sectional diagnosis labels (i.e., output score) for a selected scan may differ from the baseline label. Such potential disease progression may be significant in prodromal disease status, e.g., MCI in AD pathology.

In an embodiment, in order to avoid data leakage, partitioning the preprocessed source data 122 into training data 132, validation data 134 and testing data 136 may be performed at the level of individual patients. In other words, image data associated with a selected patient may be included in only one partition. Inclusion of the patient data 130 in the source data is configured to facilitate partitioning at the level of individual patient. The partitioning may be further configured to avoid overlap. In other words, the partitioning may be configured such that each image dataset is included in only one partition.

ANN 110 may then be trained based, at least in part, on the preprocessed source data 122 and associated partitioned data sets. For example, the training data 132 may be used to train ANN 110. The validation data 134 may then be used to validate the trained ANN 110. For example, a set of ANN parameters 112 associated with a highest validation accuracy (i.e., classification accuracy in a validation dataset) may be selected as the final ANN parameters. The testing data 136 may be used to test the trained ANN 110.

ANN training logic 108 may be configured to retrieve one or more training data sets from training data 132 included in data store 120. Input image data 140 corresponding to training input image data may then be provided to the ANN 110. The ANN 110 may be allowed to operate to produce an output score 142. The output score is one example of a classification output. The output score 142 may be compared to the corresponding cognitive status indicator, e.g. cognitive status indicator 128. One or more ANN parameters 112 may then be adjusted, e.g., until a loss function achieves a target threshold. For example, the ANN parameters 112 may be adjusted via a parameter adjust command 144 from ANN training logic 108. The training operations may be repeated to yield a plurality of sets of ANN parameters.

ANN training logic 108 may be configured to retrieve one or more validation data sets from validation data 134 included in data store 120. For each set of ANN parameters, input image data 140 corresponding to validation input image data may then be provided to the ANN 110. The ANN 110 may be allowed to operate to produce an output score 142. The output score 142 may be compared to the corresponding cognitive status indicator, e.g. cognitive status indicator 128. ANN training logic 108 may then be configured to select the ANN parameters with the highest validation accuracy. The selected ANN parameters may then correspond to ANN parameters 112 of the trained ANN. The trained ANN 110 may then be utilized to classify a new image.

Figure 1B:
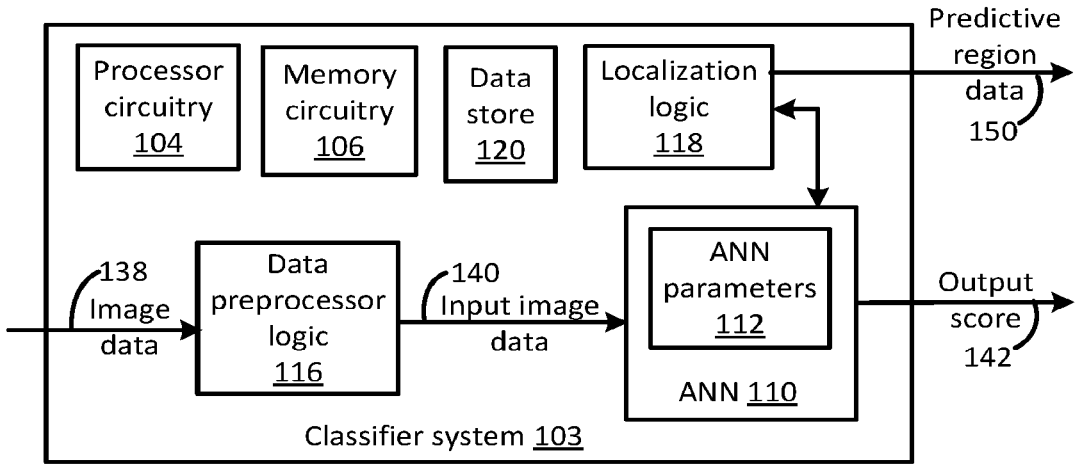
FIG. 1B illustrates a functional block diagram of a classifier system including the trained ANN of FIG. 1A.

FIG. 1B illustrates a functional block diagram 103 of a classifier system including the trained ANN 110 of FIG. 1A. Classifier system 103 includes processor circuitry 104, memory circuitry 106, trained ANN 110 that includes ANN parameters 112 and data preprocessor logic 116. Classifier system 103 is configured to receive image data 138 (i.e., patient image data) and to generate an output score 142 based, at least in part, on the image data 138. The patient image data may be acquired from a patient image storage system and preprocessed, as described herein, prior to provision to ANN 110. Patient image data corresponds to medical image data, as described herein. Similar to the operations of training system 102, data preprocessor logic 116 is configured to preprocess the image data, as described herein, to yield input image data (i.e., preprocessed patient image data) 140. Data preprocessor logic 116 may then provide the input image data 140 to the ANN 110. ANN 110 may then generate the output score 142, i.e., classification output.

Figure 2:
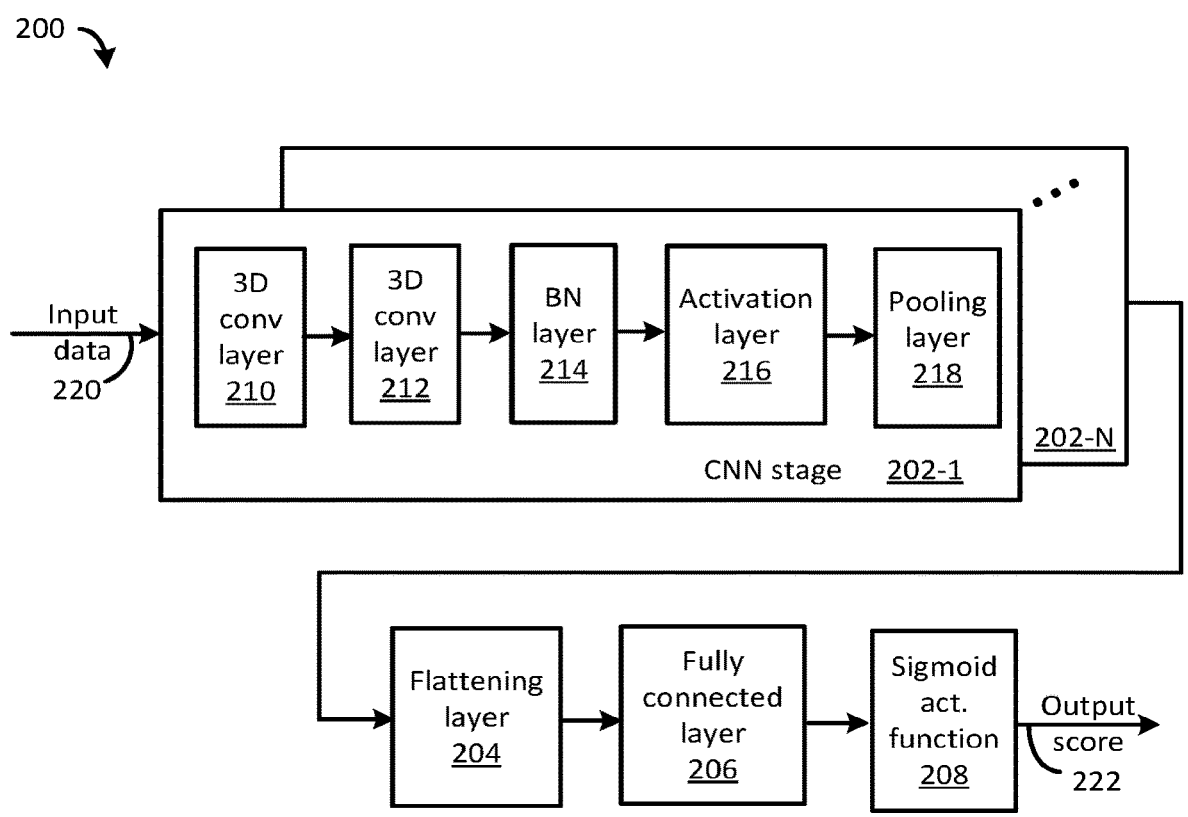
FIG. 2 illustrates a functional block diagram of one example ANN according to the present disclosure.

FIG. 2 illustrates a functional block diagram of one example ANN 200 according to the present disclosure. ANN 200 is one example of ANN 110 of FIGS. 1A and 1B. In particular, example ANN 200 corresponds to a 3D CNN. After training (and validation), ANN 200 may be configured with ANN parameters, e.g., ANN parameters 112, determined during training. ANN parameters 112 may thus correspond to CNN parameters. ANN 200 is configured to receive input data 220, for example, preprocessed patient image data. The patient image data may be acquired from a patient image storage system and preprocessed, as described herein, prior to provision to ANN 200. ANN 200 is further configured to provide as output an output score 222. The output score 222 may correspond to a classification output and may be generated based, at least in part, on the input data 220.

ANN 200 includes a number, N, CNN stages 202-1, ..., 202-N. In one nonlimiting example, N may be 5. However, this disclosure is not limited in this regard. Each CNN stage, e.g., CNN stage 202-1, includes a first 3D convolutional layer 210, a second 3D convolutional layer 212, a batch normalization layer 214, an activation layer 216, and a pooling layer 218, coupled in series. ANN 200 further includes a flattening layer 204, a fully connected layer 206 and a sigmoid activation function layer 208. The first CNN stage 202-1 is configured to receive input data 220, e.g., preprocessed patient image data. The N CNN stages 202-1, ..., 202-N are coupled in series and an output of the Nth CNN stage 202-N is coupled to the flattening layer 204. The flattening layer 204, fully connected layer 206 and sigmoid action function 208 are coupled in series. The sigmoid action function 208 may be configured to provide the output score 222 based, at least in part, on the input data 220.

In an embodiment, a general ANN architecture of ANN 110 may be related to a VGG classification architecture with a plurality of interleaved convolutional blocks and max pooling layers and increasing number of features along the depth. For example, for each CNN stage, e.g., CNN stage 202-1, convolutional layers 210, 212 may utilize a convolutional kernel size of 3×3×3, BN layer 214 may be configured to implement a batch normalization with a batch size of 5, the activation function 216 may correspond to a rectified linear unit (ReLU). The output from the last convolutional layer, i.e., CNN stage 202-N, may be flattened 204 and fed into a fully-connected (FC) layer 206 with sigmoid as the activation 208.

For example, the ANN 200 may be trained, i.e., optimized, using Adam method with cross-entropy loss function. In an embodiment, initial learning rate may be tuned in the range from $1e$-4 to $1e$-6 including [$1e$-4, $5e$-5, $2e$-5, $1e$-5, $5e$-6, $2e$-6, $1e$-6]. In one nonlimiting example, the learning rate may be set at $2e$-5. In one nonlimiting example, the ANN 200 may be implemented using Keras (a Python deep learning library) and TensorFlow (open source machine learning platform). As an early stopping criteria, a patience parameter on validation accuracy may be set to 10 epochs. Weight l2 regularization (also known as weight decay) may be implemented to prevent overfitting with a factor of 1:0. In this example, N, the number of stages is five. However, this disclosure is not limited in this regard. The feature dimension of the first layer is 16 and increases by a factor of 2 in each subsequent stage. Thus, ANN 200 may be trained.

Turning now to FIGS. 1A and 1B, in some embodiments, training system 102 and/or classifier system 103 may include localization logic 118. Localization logic 118 is configured to identify a most predictive image region based, at least in part, on an ANN parameter associated with the trained ANN. For example, the ANN parameter may be determined based, at least in part, on training operations and/or analysis of the trained ANN. Localization logic 118 may be configured to generate a 3D class activation map to visualize predictive contributions of a plurality of brain regions to classification operations. In particular, localization logic 118 is configured to implement a gradient-weighted class activation map (grad-CAM) with a rectified linear unit (ReLU) gradient modifier and rescaled generated CAM with min-max normalization. Grad-CAM is configured to utilize gradient information flowing into the last convolutional layer of an ANN to understand the importance of each neuron in a decision of interest. It may be appreciated that since the map can be generated individually, it has the potential to be used as an individual neuroanatomical validity report without sacrificing the prediction power of whole brain based prediction model. For example, an average class activation map for all AD patients may be generated to demonstrate an average "attention" of the algorithm. Average class activation maps may be generated for a further refined sub-population within a population.

In some embodiments, localization logic 118 may be configured to perform ablation analyses that focus on part of the input data. In one nonlimiting example, the classification operations may utilize two-dimensional (2D) CNN with the input being three consecutive slices as three channels. It may be appreciated that this design takes the inter-subject alignment precision into consideration (i.e. not extracting just one slice) and is configured to provide relative similarity among different channels (i.e. not extracting five slices). For example, the 2D CNN network architecture may correspond to the architecture of ANN 200 except that the 3D operations are all replaced with the corresponding 2D operations.

In some embodiments, localization logic 118 may be configured to perform brain lobe based classification. A slice-based regional analysis method may provide a way to investigate the predictive regions of the classification from an imaging perspective, as the coordinate planes are imaging planes. Each slice represents a mixture of multiple regions located at a certain spatial level. It may be relatively more appealing to generate neuroanatomically meaningful regions and perform classification focusing on these regions separately. A probabilistic spatial distribution of different regions was derived from the affinely co-registered FreeSurfer segmentations from 1,495 scans. An occurrence probability of 0.5% was used as the threshold for the lobe mask generation. The definition of lobes in FreeSurfer segmentation nomenclature is referenced in FreeSurfer website. Performing a lobe-level ablation analysis is facilitated by the fact that the brain lobes are functionally and structurally distinct units.

Thus, an ANN may be trained based, at least in part, on longitudinal patient data. The trained ANN may be analyzed to identify a most predictive region in an input image data. The most predictive region may then point to a region in the brain that may be associated with the existence and progression of neurological disease.

FIG. 3 is a flowchart 300 of example ANN training operations consistent with several embodiments of the present disclosure. In particular, flowchart 300 illustrates training an ANN based, at least in part, on a training data set. The operations of flowchart 300 may be performed by, for example, training system 102 (e.g., ANN training logic 108, data preprocessor logic 116, ANN 110 and/or localization logic 118) of FIG. 1A.

Operations of flowchart 300 may begin with acquiring source data at operation 302. The source data may include a plurality of data sets, each data set including image data, a cognitive status indicator and patient data, as described herein. The image data, i.e., medical image data, may include, but is not limited to, MRI image data, MRI T1-weighted image data, MRI T2-weighted image data, CT, CBV image data, CBF image data, MTT image data, PET image data, and SPECT image data. The source data may then be preprocessed into preprocessed source data at operation 304. The preprocessed source data may then be partitioned into training, validation and testing data sets at operation 306. The partitioning may be based, at least in part, on the patient data and is configured to partition such that image data for a selected patient is included in one partition. The partitioning is further configured to avoid overlap, as described herein. Operation 308 includes training the ANN based, at least in part, on the training data set. For example, the training may include adjusting one or more parameters of the ANN based, at least in part, on a data set and a corresponding output score. In some embodiments, a most predictive image region may be identified at operation 310. The most predictive image region corresponds to an anatomical region in the image data whose features contributed to an output classification, as described herein. Program flow may then continue at operation 312.

Thus, an ANN may be trained based, at least in part, on source data that includes longitudinal data from at least one patient.

FIG. 4 is a flowchart 400 of example neurological disease classification operations consistent with several embodiments of the present disclosure. In particular, flowchart 400 illustrates utilizing a trained ANN to provide a neurological disease status indicator. The ANN may be trained according to the operations of flowchart 300 of FIG. 3. The operations of flowchart 400 may be performed by, for example, classifier system 103 (e.g., data preprocessor logic 114, ANN 110 and/or localization logic 118) of FIG. 1B.

Operations of flowchart 400 may begin with acquiring patient image data at operation 402. The patient image data may include image data, and the image data may correspond to medical image data, as described herein. The patient image data may then be preprocessed into input image data at operation 404. The input image data may then be provided to a trained ANN at operation 406. Operation 408 may include generating, by the trained ANN, a classification output based, at least in part, on the input image data. In some embodiments, a most predictive image region may be identified at operation 410. Program flow may then continue at operation 412.

Thus, a trained ANN may be used to provide a current patient status and/or disease progression indicator.

EXAMPLE

Figure 5:
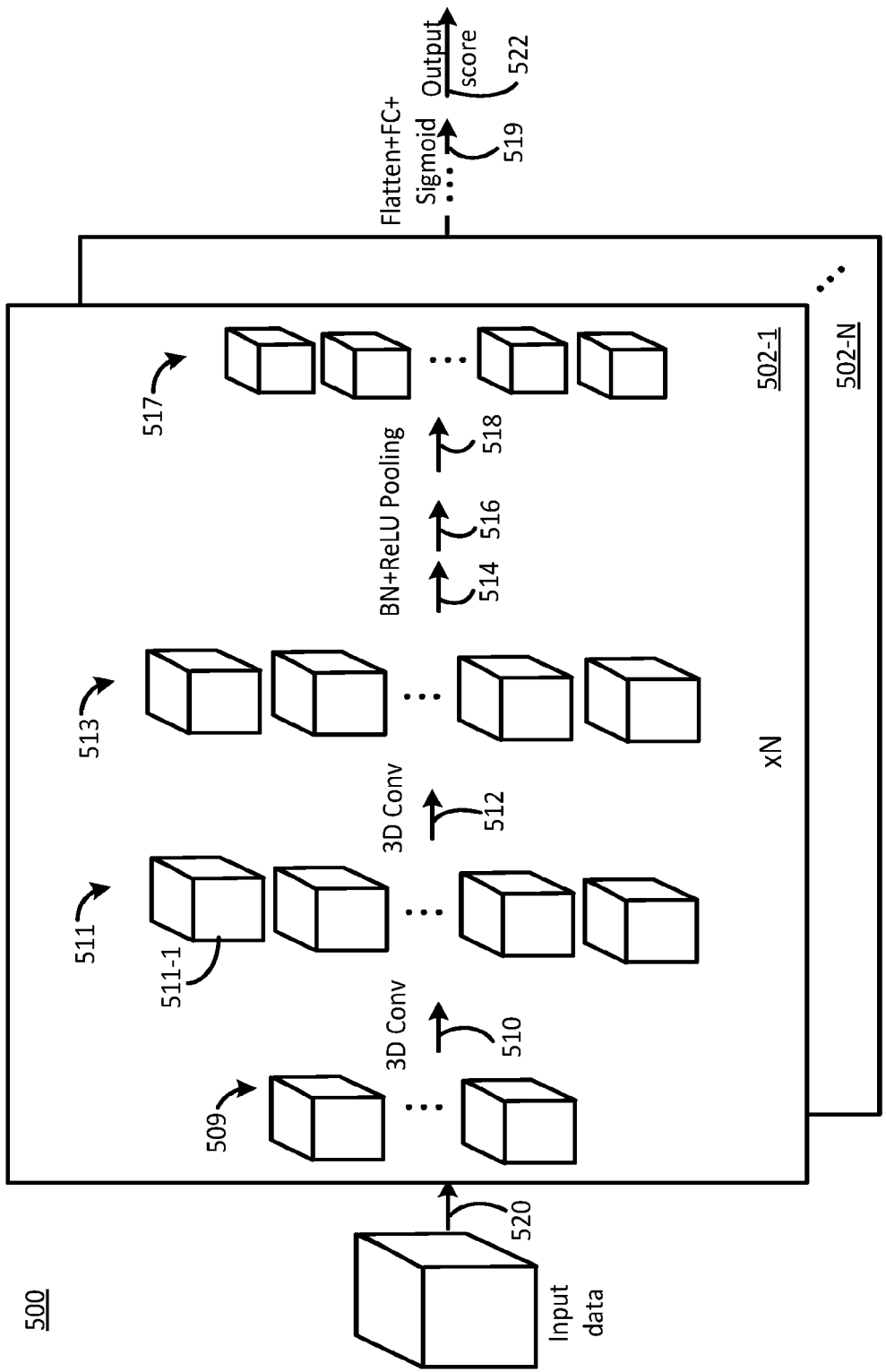
FIG. 5 is a sketch illustrating operations of one example three dimensional (3D) CNN consistent with one embodiment of the present disclosure.

FIG. 5 is a sketch illustrating operations of one example three dimensional (3D) CNN 500 consistent with one embodiment of the present disclosure. Example CNN 500 may correspond to the example ANN 200 of FIG. 2. Example CNN 500 is configured to receive input image data 520, and to provide as output a classification score 522, as described herein. Example CNN 500 includes a number N CNN stages 502-1, ..., 502-N coupled in series. Example CNN 500 further includes plurality 519 of layers that include a flatten layer followed by a fully connected layer followed by a sigmoid activation function. The plurality 519 of layers is coupled to the Nth CNN stage 502-N. Each CNN stage, e.g., CNN stage 502-1, includes two convolutional layers 510, 512 followed by a batch normalization layer 514. The batch normalization layer 514 is followed by an activation layer (a rectified linear unit, in this example) 516 followed by a pooling layer 518.

Each CNN stage, e.g., CNN stage 502-1 includes a plurality of sets 509, 511, 513 and 517 of 3D feature maps. Each cubic, e.g. cubic 511-1, represents one 3D feature map. A size of each cube reflects the spatial dimension of the feature map. A number of cubes reflects the number of feature maps (i.e., channel dimension). At each subsequent CNN stage, in the series of CNN stages 502-1, ..., 502-N, the number of features is configured to increase and the spatial dimension is configured to decrease.

Experimental Data
AD Classification

The classification performance in an AD versus CN task of classifier system 103 (that included example 3D CNN 200) was evaluated both on unique MRI sessions and the baseline scans of unique subjects. Classifier system 103 achieved 0.980 AUROC (area under the curve receiver operating characteristic) and 93.3% accuracy when evaluated on unique MRI sessions, and 0.990 AUROC and 96.6% accuracy when evaluated on the baseline scans of unique subjects. It is contemplated that the relatively high overall classification accuracy of classifier system 103 may support subsequent results investigating regional attribution.

Application to MCI Progression Prediction

The classification performance of classifier system 103 (that included example 3D CNN 200) trained exclusively on AD and CN patients may be used post hoc to differentiate among those MCI patients who will and will not progress in the near term to AD. The ADNI dataset contains MCI patients whose subsequent progression or not to AD has been noted longitudinally. Ideally, a classifier system, e.g., classifier system 103, might be trained exclusively on MCI patients whose subsequent progression status has been observed, directly learning to distinguish AD's prodromal stage from other causes of MCI. However, the ADNI dataset does not contain sufficient MCI patients (around 600) to train such a classifier. Although the subset of MCI patients is too small for direct training, it is sufficiently large to serve as an evaluation set.

To determine the usefulness of classifier system 103, trained as an AD vs. CN classifier, for recognizing those MCI cases that will progress to AD, MCI patient data was processed through an AD vs. CN binary classifier, interpreting a higher probability of AD as more likely to progress to AD and a higher probability of CN as less likely to progress. For this experiment, the AD vs. CN classifier was trained using only baseline scans from subjects diagnosed as either AD or CN at baseline achieving an AUROC of 0.973 on i.i.d. holdout data. The evaluation set of MCI patients was then provided to the classifier, achieving an AUROC of 0.787 (0.808 when including only MCI patients who progressed or stayed stable within 3 years), matching state-of-the-art performance while using structural MM data only. It should be noted that this evaluation procedure applies the CNN out-of-sample to a subset of patients that are not represented in the training set. In general, machine learning are liable to break under distribution shift and thus the performance, despite matching the previous state-of-the-art, might be far from the ceiling of what may be achieved given adequate data. Likely, in the future, given a large dataset of MCI patients, sufficient for training a progression prediction classifier directly, a higher predictive accuracy may be achieved. The results might suggest that the neuroanatomical pattern of MCI partially lies on the normal-to-AD continuum.

Localization

The localization approaches, as described herein, including class activation maps, slice and brain lobe level ablation experiments, suggest that the hippocampal formation may be most predictive of AD. ANNs may be considered to be black boxes, useful for pattern recognition and classification but less amenable to interpretation. The trade-offs between separability and interpretability have been discussed in multivariate based analysis, and is becoming more obvious with the more complex architecture of deep neural networks.

Through a combination of evidence produced by both heuristic saliency-based interpretations and rigorous region and lobar level ablation studies (e.g., 2D slice-based models and lobe-masking experiments), ANNs can be used not only for predictions but also to provide insights with likely neurobiological consequence.

While the hippocampal region may appear predictive of AD, all regions offer some predictive value. Thus, in practice, for building tools to aid in the diagnosis of AD, and for predicting progression to AD among the MCI population, CNNs that act upon whole brain volumes should be trained. For example, CNNs acting upon whole brain volumes achieved the best AUC as compared to those acting upon any single slice or lobe.

Classifying the Dementia Stage of Alzheimer's Disease

The classifier system 103 was trained, validated, and tested on 975 MRI scans repeatedly acquired in patients in the dementia stage of AD, versus 1943 MRI scans repeatedly acquired from healthy controls. In the test set, a 'deep learning MRI' score (i.e., output score) was derived for each scan from the classifier system, with the score reflecting the probability of each scan having AD. A receiver operating characteristic (ROC) analysis revealed that the deep learning MRI scores accurately classified AD dementia vs. healthy controls with an AUROC (area under the receiver operating characteristics curve) of 0.973.

An AD 'class activation map' was generated to determine whether the deep learning MRI scores derived from the model were regionally dominated. The deep learning MRI scores are dominated by alterations in voxel signal intensity that localized to anterior medial temporal lobe, in the vicinity of the anterior entorhinal cortex and hippocampus. It is noted that while the class activation map localized to the left more than the right anterior medial temporal lobe, contralateral areas emerged with lowered thresholding.

Classifying the Prodromal Stage of Alzheimer's Disease

From ADNI, a cohort of participants were identified who were diagnosed with MCI at baseline and who had a complete set of CSF amyloid and tau biomarkers and structural MRI (N=582). Among these, 205 participants progressed to AD dementia at follow up ('MCI progression' group), and thus had prodromal AD at baseline, while 179 participants remained MCI stable for at least 4 years ('MCI stable' group). The dementia-derived deep learning classifier (e.g., classifier system 103, including 3D CNN 200) was used to generate deep learning MRI scores on each individual case.

ROC analyses revealed that the deep learning MRI score outperformed all other biomarkers in classifying the MCI-stable from the MCI-progression group. The AUROC of deep learning MRI score was 0.788 (Accuracy at Youden (ACC)=75%), superior to CSF A$\beta$ (AUROC=0.702 ACC=66.7%, significantly lower than the deep learning MRI score, p=0.0141), CSF tau (AUROC=0.682, ACC=66.4%, p=0.0161), CSF tau/A$\beta$ (AUROC=0.703, ACC=68.5%, p=0.0161); superior to MRI-based measures of hippocampal volume (AUROC=0.733, ACC=67.7%, p=0.0484), entorhinal cortex volume (AUROC=0.64, ACC=62.5%, p=2.01E-6), and entorhinal cortex thickness (AUROC=0.685, ACC=64.1%, p=1.71E-4); and, finally, superior to Mini-Mental State Exam (AUROC=0.648, ACC=63.3%, p=6.70E-5), and to neuropsychological measure most sensitive to the early stages of AD, the RAVLT retention score (AUROC=0.686, ACC=67.7%, p=2.28E-3).

The deep learning MRI score was found to outperform or perform as well when tested in a subset of participants in whom additional PET-based biomarkers were available—FDG-PET that by measuring parietal cortex metabolism is considered a biomarker of neurodegeneration, and AV45-PET, which by using an amyloid radioligand is a biomarker of amyloid pathology. In this subset, the deep learning MM score classified prodromal AD with an AUROC=0.815 (ACC=78.6%), compared to the AUROC of 0.782 (for PDG-PET (ACC=75.4%) and 0.751 (ACC=71.4%) for amyloid-PET, although the differences were not statistically significant.

Predicting Progression to Alzheimer's Disease Dementia

Survival analyses were performed to determine which biomarker best predicted progression to AD dementia among the MCI groups. Results revealed that compared to other biomarkers, the deep learning MRI score best predicted time to conversion to AD dementia. The deep learning MRI scores showed better prediction capability ($|z|=11.0$, p=4.35E-28) than CSF biomarkers of amyloid and tau pathology (A$\beta|z|=6.37$, p=1.87E-10, tau$|z|=5.70$, =1.18E-08, tau/A$\beta|z|=5.41$, p=6.29E-08); than MRI-based biomarkers of neurodegeneration (hippocampal volume$|z|=8.80$, p=1.35E-18, entorhinal volume$|z|=6.02$, p=1.75E-09, entorhinal thickness$|z|=7.42$, p=1.21E-13); and, than behavioral measures (MMSE|z|=5.72, p=1.07E-08, RAVLT retention|z|=6.88, p=6.12E-12). Similarly, in the subset in whom the additional PET biomarkers were available the deep learning MRI score (|z|=9.04, p=1.40E-19) outperformed or performed as well as FDG-PET (|z|=9.11, p=8.14E-20) and AV45-PET |z|=7.12, p=1.04E-12).

Thus, systems and methods according to the disclosed subject matter may include a neurological disease diagnosis framework based on a deep ANN model using medical imaging and corresponding medical image data, empowered with the inclusion of longitudinal scans. In one nonlimiting example, the framework, as described herein, demonstrates relatively high classification performance in Alzheimer's disease (AD) versus cognitive normal (CN) using structural MRI image data. Continuing with this example, systems and methods according to the disclosed subject matter demonstrate relatively high accuracy in mild cognitive impairment (MCI) progression prediction applying the model trained on AD vs. CN classification to the MCI subgroup.

FreeSurfer is a software package for the analysis and visualization of structural and functional neuroimaging data from cross-sectional or longitudinal studies, developed by the Laboratory for Computational Neuroimaging at the Athinoula A. Martinos Center for Biomedical Imaging, Charlestown, Massachusetts FSL is a library of analysis tools for FMRI, MRI and DTI brain imaging data, created by the Analysis Group, FMRIB, Oxford, United Kingdom. FSL FLIRT (FMRIB's Linear Image Registration Tool) is a fully automated robust and accurate tool for linear (affine) intra- and inter-modal brain image registration.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hardwired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Processor circuitry 104 may include, but is not limited to, a single core processing unit, a multicore processor, a graphics processing unit, a microcontroller, an application-specific integrated circuit (ASIC), a field programmable gate array (FPGA), a programmable logic device (PLD), etc. Memory circuitry 106 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory 106 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method for classifying a neurological disease status, comprising:
    acquiring, by a data preprocessor logic configuration, patient image data;
    electronically preventing overfitting by an artificial neural network (ANN) by enriching the patient image data through an inclusion of a plurality of transformations of the patient image data, the plurality of transformations including longitudinal source data comprising a time series of image data for a patient;
    training the ANN on the enriched patient image data, the training comprising:
        inputting a training data set from the enriched patient image data;
        generating an output score based on the training data set;
        comparing the output score to a corresponding cognitive status indicator; and
        upon a determination that a loss function for the output score does not meet a target threshold, adjusting at least one ANN parameter based on the comparison; and
    generating, by the trained ANN, a classification output based, at least in part, on testing data from the patient image data, the classification output corresponding to a neurological disease status of the patient.

2. The method of claim 1, further comprising preprocessing, by the data preprocessor logic configuration, the patient image data to yield input image data, the classification output generated based, at least in part, on the input image data.

3. The method of claim 1, further comprising identifying, by a localization logic configuration, a most predictive image region based, at least in part, on an ANN parameter associated with the trained ANN.

4. The method of claim 1, wherein the longitudinal source data comprises a plurality of source image data sets from same selected patient, wherein the longitudinal source data is partitioned into training data, validation data and test data, and wherein the partitioning occurs at a level of the same selected patient.

5. The method of claim 1, wherein the image data comprises at least one of magnetic resonance imaging (MRI) image data, MRI T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, or single-photon emission computerized tomography (SPECT) image data.

6. The method of claim 1, wherein the neurological comprises neurodegenerative diseases and non-neurodegenerative diseases, wherein each neurodegenerative disease comprises at least one of Alzheimer's disease, amyotrophic lateral sclerosis (ALS), frontotemporal dementia (FTD) or Parkinson's disease, and wherein each of the non-neurodegenerative diseases comprises cerebrovascular disease, epilepsy, or stroke.

7. The method of claim 1, wherein the neurological disease corresponds to Alzheimer's disease and the classification output is comprises at least one of Alzheimer's disease (AD), prodromal AD, mild cognitive impairment (MCI) or cognitively normal (CN).

8. The method of claim 1, wherein the ANN is comprises at least one of CNN (convolutional neural network), VGG-Net (Visual Geometry Group neural network), ResNet (residual network), or DenseNet (densely connected convolutional networks).

9. The method of claim 1, wherein the ANN is a three-dimensional convolutional neural network (3D CNN), wherein the 3D CNN comprises a number, N, CNN stages coupled in series, wherein each of the CNN stages comprises a first 3D convolutional layer, a second 3D convolutional layer, a batch normalization layer, an activation layer, and a pooling layer, coupled in series, and wherein the 3D CNN further comprises a flattening layer, a fully connected layer and a sigmoid activation function layer.

10. The method of claim 1, further comprising,
identifying, by the trained ANN, a most predictive region in the patient image data, wherein the generated classification output is based on the identified most predictive region.

11. The method of claim 1, wherein the patient image data comprise 3-dimensional volumetric digital image data.

12. A neurological disease classifier system, comprising:
a data preprocessor logic configuration configured to acquire patient image data; and
a training system configured to:
electronically preventing overfitting by an artificial neural network (ANN) by enriching the patient image data through an inclusion of a plurality of transformations of the patient image data, the plurality of transformations including longitudinal source data comprising a time series of image data for a patient;
train the ANN on the enriched patient image data, the training comprising:
inputting a training data set from the enriched patient image data;
generating an output score based on the training data set;
comparing the output score to a corresponding cognitive status indicator; and
upon a determination that a loss function for the output score does not meet a target threshold, adjusting at least one ANN parameter based on the comparison; and
generate by the trained ANN, a classification output based, at least in part, on testing data from the patient image data, the classification output corresponding to a neurological disease status of the patient.

13. The system of claim 12, wherein the data preprocessor logic configuration is further configured to preprocess the patient image data to yield input image data and the classification output is generated based, at least in part, on the input image data.

14. The system of claim 12, further comprising a localization logic configuration configured to identify a most predictive image region based, at least in part, on an ANN parameter associated with the trained ANN.

15. The system of claim 12, wherein the longitudinal source data comprises a plurality of source image data sets from same selected patient, wherein the longitudinal source data is partitioned into training data, validation and test data, and wherein the partitioning occurs at a level of the same selected patient.

16. The system according to claim 12, wherein the image data is comprises at least one of magnetic resonance imaging (MRI) image data, MRI T1-weighted image data, MRI T2-weighted image data, computed tomography (CT) image data, cerebral blood volume (CBV) image data, cerebral blood flow (CBF) image data, mean transit time (MTT) image data, positron emission tomography (PET) image data, or single-photon emission computerized tomography (SPECT) image data.

17. The system according to claim 12, wherein the neurological disease comprises neurodegenerative diseases and non-neurodegenerative diseases, wherein each neurodegenerative disease comprises at least one of Alzheimer's disease, amyotrophic lateral sclerosis (ALS), frontotemporal dementia (FTD) or Parkinson's disease, and wherein each of the non-neurodegenerative diseases comprises cerebrovascular disease, epilepsy, or stroke.

18. The system according to claim 12, wherein the neurological disease corresponds to Alzheimer's disease and the classification output is comprises at least one of Alzheimer's disease (AD), prodromal AD, mild cognitive impairment (MCI) or cognitively normal (CN).

19. The system according to claim 12, wherein the ANN is comprises at least one of CNN (convolutional neural network), VGGNet (Visual Geometry Group neural network), ResNet (residual network), or DenseNet (densely connected convolutional networks).

20. The system according to claim 12, wherein the ANN is a three-dimensional convolutional neural network (3D CNN), wherein the 3D CNN comprises a number, N, CNN stages coupled in series, wherein each of the CNN stages comprises a first 3D convolutional layer, a second 3D convolutional layer, a batch normalization layer, an activation layer, and a pooling layer, coupled in series, and wherein the 3D CNN further comprises a flattening layer, a fully connected layer and a sigmoid activation function layer.

21. A neurological disease classification device comprising:
a data preprocessor logic configuration configured to acquire patient image data; and
a training system configured to:
electronically prevent overfitting by an artificial neural network (ANN) by enriching the patient image data through an inclusion of a plurality of transformations of the patient image data, the plurality of transformations including longitudinal source data comprising a time series of image data for a patient;
train the ANN on the enriched patient image data, the training comprising:
inputting a training data set from the enriched patient image data;
generating an output score based on the training data set;
comparing the output score to a corresponding cognitive status indicator; and upon a determination that a loss function for the output score does not meet a target threshold, adjusting at least one ANN parameter based on the comparison; and generate by the trained ANN, a classification output based, at least in part, on testing data from the patient image data, the classification output corresponding to a neurological disease status of the patient.

22. A computer readable storage device having stored thereon executable instructions that, when executed by one or more processors, causes a computer processing arrangement to perform procedures comprising:

acquiring, by a data preprocessor logic configuration, patient image data;

electronically preventing overfitting by an artificial neural network (ANN) by enriching the patient image data through an inclusion of a plurality of transformations of the patient image data, the plurality of transformations including longitudinal source data comprising a time series of image data for a patient;

training the ANN on the enriched patient image data, the training comprising:
 inputting a training data set from the enriched patient image data;
 generating an output score based on the training data set;
 comparing the output score to a corresponding cognitive status indicator; and
 upon a determination that a loss function for the output score does not meet a target threshold, adjusting at least one ANN parameter based on the comparison; and generating, by the trained ANN, a classification output based, at least in part, on testing data from the patient image data, the classification output corresponding to a neurological disease status of the patient.

* * * * *